US00PP14607P29

(12) United States Plant Patent
Lamb et al.

(10) Patent No.: US PP14,607 P2
(45) Date of Patent: Mar. 16, 2004

(54) SPATHIPHYLLUM PLANT NAMED '6598-1'

(50) Latin Name: *Spathiphyllum*
Varietal Denomination: 6598-1

(75) Inventors: Ann Elizabeth Lamb, Sebring, FL (US); David R. Lilly, Boynton Beach, FL (US)

(73) Assignee: Twyford International Inc., Santa Paula, CA (US)

( * ) Notice: Subject to any disclaimer, the term of this patent is extended or adjusted under 35 U.S.C. 154(b) by 0 days.

(21) Appl. No.: 10/377,500

(22) Filed: Feb. 28, 2003

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Spathiphyllum plant named '6598-1', characterized by its large, upright, somewhat outwardly spreading and symmetrical plant habit; glossy, broad, dark green and rugose leaves with undulate leaf margins; rapid growth rate; freely flowering habit; large white-colored spathes that are positioned just above the foliage on erect peduncles; and good postproduction longevity.

3 Drawing Sheets

Botanical classification/cultivar designation: Spathiphyllum hybrid cultivar 6598-1.

BACKGROUND OF THE INVENTION

The present Invention relates to a new and distinct cultivar of Spathiphyllum plant, botanically known as Spathiphyllum hybrid, and hereinafter referred to by the cultivar name 6598-1.

The new cultivar is a product of a planned and controlled breeding program conducted by the Inventors in Apopka, Fla. The objective of the breeding program is to create new Spathiphyllum cultivars with improved plant habit, dark green foliage and rapid growth rate.

The new cultivar originated from a cross-pollination made by the Inventors on Feb. 9, 1998 of the Spathiphyllum hybrid cultivar Sparkle, disclosed in U.S. Plant Pat. No. 8,367, as the female or seed parent and the Spathiphyllum hybrid cultivar Sweet Pablo, disclosed in U.S. Plant Pat. No. 10,817, as the male or pollen parent. The cultivar 6598-1 was discovered and selected by the Inventors as a plant within the progeny of the stated cross-pollination in a controlled environment in Homestead, Fla., on Sep. 23, 1999.

Asexual propagation of the new cultivar by tissue culture since September, 1999, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of '6598-1'. These characteristics in combination distinguish '6598-1', as a new and distinct Spathiphyllum cultivar:

1. Large, upright, somewhat outwardly spreading and symmetrical plant habit.
2. Glossy, broad, dark green and rugose leaves with undulate leaf margins.
3. Rapid growth rate.
4. Freely flowering habit.
5. Large white-colored spathes that are positioned just above the foliage on erect peduncles.
6. Good postproduction longevity.

Plants of the new Spathiphyllum differed from plants of the female parent, the cultivar Sparkle, when grown in side-by-side comparisons in Apopka, Fla., in the following characteristics:

1. Plants of the new Spathiphyllum were much larger than plants of the cultivar Sparkle.
2. Leaves of plants of the new Spathiphyllum were broader and thicker than leaves of plants of the cultivar Sparkle.
3. Spathes of plants of the new Spathiphyllum were larger than spathes of plants of the cultivar Sparkle.
4. Spathes of plants of the new Spathiphyllum were ovate in shape whereas spathes of plants of the cultivar Sparkle were elliptic in shape.

Plants of the new Spathiphyllum differed from plants of the male parent, the cultivar Sweet Pablo, when grown in side-by-side comparisons in Apopka, Fla., in the following characteristics:

1. Plants of the new Spathiphyllum were larger and taller than plants of the cultivar Sweet Pablo.
2. Leaves of plants of the new Spathiphyllum were darker green, larger, broader and more rugose than leaves of plants of the cultivar Sweet Pablo.
3. Leaves of plants of the new Spathiphyllum were elliptic in shape whereas leaves of plants of the cultivar Sweet Pablo were longer and lanceolate in shape.
4. Plants of the new Spathiphyllum had larger spathes than plants of the cultivar Sweet Pablo.
5. Spathes of plants of the new Spathiphyllum were ovate in shape whereas spathes of plants of the cultivar Sweet Pablo were lanceolate in shape.

Plants of the new Spathiphyllum can be compared to plants of the Spathiphyllum cultivar Linda, not patented. In side-by-side comparisons conducted in Apopka, Fla., plants of the new Spathiphyllum differed from plants of the cultivar Linda in the following characteristics:

1. Plants of the new Spathiphyllum were faster-growing than plants of the cultivar Linda.
2. Leaves of plants of the new Spathiphyllum were broader, thicker, more rugose, darker green, shinier and more abundant than leaves of plants of the cultivar Linda.
3. Spathes of plants of the new Spathiphyllum were held just above the foliage whereas spathes of plants of the cultivar Linda were held well above the foliage.

Plants of the new Spathiphyllum can also be compared to plants of the Spathiphyllum cultivar Miss Mabel, disclosed in U.S. Plant Patent application filed concurrently. In side-by-side comparisons conducted in Apopka, Fla., plants of the new Spathiphyllum differed from plants of the cultivar Miss Mabel in the following characteristics:

1. Plants of the new Spathiphyllum were larger than plants of the cultivar Miss Mabel.
2. Leaves of plants of the new Spathiphyllum were larger and broader than leaves of plants of the cultivar 6598-1.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph on the first sheet comprises a side perspective view of a typical 11-month old plant of '6598-1' grown in a 25-cm container.

The photograph on the second sheet comprises a close-up view of a typical mature inflorescence and a fully developed inflorescence of '6598-1'.

The photograph at the top of the third sheet comprises a close-up view of the upper leaf surface of a typical plant of '6598-1'.

The photograph at the bottom of the third sheet comprises a close-up view of the lower leaf surface of a typical plant of '6598-1'.

DETAILED BOTANICAL DESCRIPTION

The aforementioned photographs and following observations, measurements and comparisons describe 10-month old plants (from planting rooted tissue-cultured plantlets) grown in Homestead, Fla., in a polypropylene-covered shadehouse and under commercial production conditions in 20-cm containers. During the production of the plants, day temperatures ranged from 70 to 90° F., night temperatures ranged from 65 to 75° F., and light levels were about 1,500 to 2,000 foot-candles.

In the following description, color references are made to The Royal Horticultural Society Colour Chart, 1995 Edition, except where general terms of ordinary dictionary significance are used.

Botanical classification: Spathiphyllum hybrid cultivar 6598-1.

Parentage:

*Female parent.*—Spathiphyllum hybrid cultivar Sparkle, disclosed in U.S. Plant Pat. No. 8,367.

*Male parent.*—Spathiphyllum hybrid cultivar Sweet Pablo, disclosed in U.S. Plant Pat. No. 10,817.

Propagation:

*Type.*—By tissue culture.

*Time to initiate roots on a tissue-cultured cutting.*—Summer: About 6 to 8 days at 70 to 90° F. day temperature and 65 to 75° F. night temperature. Winter: About 7 to 10 days at 70 to 90° F. day temperature and 65 to 75° F. night temperature.

*Time to produce a fully-rooted tissue-cultured plantlet.*—Summer: About 70 days at 70 to 90° F. day temperature and 65 to 75° F. night temperature. Winter: About 84 days at 70 to 90° F. day temperature and 65 to 75° F. night temperature.

*Root description.*—Thick, fleshy; lateral branch roots, fine; white in color.

Plant description:

*Plant shape.*—Upright, somewhat outwardly spreading and symmetrical plant habit; large in stature.

*Growth habit.*—Erect when young, becoming somewhat outwardly arching as leaves develop. Freely clumping and full appearance; about nine clumps per plant. Plants of the new Spathiphyllum are typically grown in 25 to 35-cm containers.

*Plant height.*—About to 76 to 85 cm from soil level to top of leaf plane and about 86 to 98 cm from soil level to spathe apices.

*Plant spread.*—About 100 to 109 cm.

*Growth rate.*—Rapid growth rate; from tissue-cultured plantlets, about ten months are required to produce finished flowering plants in 25-cm containers and about twelve months are required to produce finished flowering plants in 35-cm containers.

*Foliage description.*—Length: About 39 to 43 cm. Width: About 18 to 20 cm. Shape: Broadly ovate to elliptic. Apex: Acuminate. Base: Obtuse. Margin: Entire; moderately undulate. Aspect: Initially upright, then perpendicular to the petiole; eventually oldest leaves outwardly arching; curved downward towards the apex. Midrib curved over the length of the leaf. Surface: Rugose; midrib and lateral veins sunken on upper surface and prominent on lower surface. Texture, upper and lower surfaces: Leathery, smooth, glabrous, durable and flexible. Venation pattern: Pinnate. Number of lateral veins per leaf: About 20 pairs. Color: Young and fully expanded leaves, upper surface: 139A; glossy. Young and fully expanded leaves, lower surface: 137C. Midrib, upper surface: 137B. Midrib, lower surface: 146C to 145C. Petiole: Length: About 45 to 58 cm. Diameter, just below the geniculum: About 6 cm. Petiole sheath, length: About 30 to 44 cm; about 7 cm between the top of the petiole sheath and the base of the geniculum. Petiole sheath, diameter: About 1.4 cm. Petiole sheath, apex: Bluntly rounded. Geniculum length: About 7 cm. Geniculum diameter: About 7 mm. Geniculum aspect: Straight to curved. Color: Petiole: 137B. Petiole sheath: 146D streaked with 137B. Geniculum: 146C tinged with 147C.

Inflorescence description:

*Inflorescence arrangment/quantity.*—Concave spathes with spadices held just above the foliage on erect peduncles. Freely flowering; typically about five open spathes per plant at one time; inflorescences arise from the petiole sheath.

*Time to flower.*—Inflorescences are initiated in the winter and early spring in Homestead, Fla.

*Inflorescence longevity.*—Spathes generally maintain white color for about four weeks on the plant. As cut flowers, spathes maintain good substance for about seven days.

*Fragrance.*—Moderately fragrant, sweet, typical of Spathiphyllum; most notable in the morning.

*Inflorescence buds.*—Length: About 15 cm. Diameter: About 1.8 cm. Shape: Spindle-shaped. Color: 155A; midrib, 145A to 145B; lateral veins, 155A; at the apex, 146D.

*Spathe.*—Length: About 18 to 24 cm. Width: About 9.5 to 11.5 cm. Depth: About 2.5 cm. Shape: Ovate. Apex: Acuminate; twisted. Base: Cuneate, oblique. Aspect: Concave. Color: Front surface: 155D; midrib, 155D tinged with 191D; apex, 155D tinged with 146C. Back surface: 155D; midrib, 144A to 144B streaked with 145B; apex, 155D tinged with 146B. Front surface with subsequent development: 144A with 145A streaked with 155D; midrib, 147D; apex, 137D. With development, color becoming entirely darker and more green than, but closest to 144A. Back surface with subsequent development: 145A to 146B streaked with 155D; midrib, 137C streaked with 146C; apex, 137C. With development, becoming entirely 137C.

*Spadix.*—Length: About 10 cm. Diameter: About 1.5 cm. Color: 158A gradually becoming closer to 137A with development. Quantity of flowers: About 400 per spadix. Pistillate flowers extend about 2 mm beyond the staminate flowers. Pollen: Moderate. Pollen color: 158D darkening to 158A with development. Pistils: Conical; 158A in color.

*Peduncle.*—Length: About 65 to 71 cm. Diameter: About 7 mm. Color: 137C to 137D.

*Fruit.*—Type: Berry. Length: About 8 mm. Diameter: About 6 mm. Shape: Elliptic. Color: Darker than, but closest to 137A; with subsequent development, tinged with 150D.

*Seed.*—Quantity per fruit: About one to five. Quantity per inflorescence: About 500 or more. Length: About 3 mm. Shape: Reniform. Color: Light brown.

Disease/pest resistance: Plants of the new Spathiphyllum have not been observed to be resistant to pathogens or pests common to Spathiphyllum.

Temperature tolerance: Plants of the new Spathiphyllum have been observed to tolerate temperatures from 45 to 104° F.

It is claimed:

1. A new and distinct cultivar of Spathiphyllum plant named '6598-1', as illustrated and described.

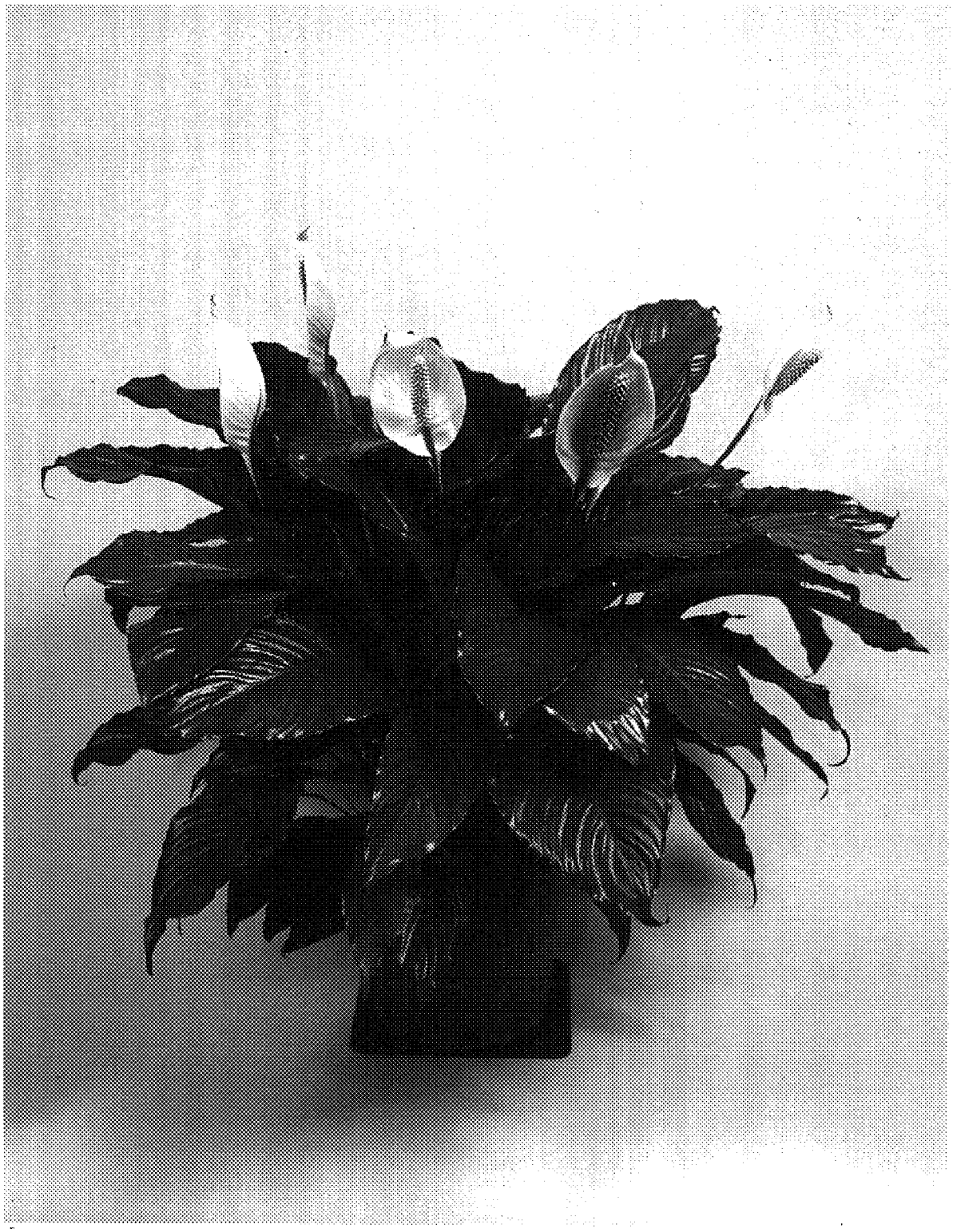

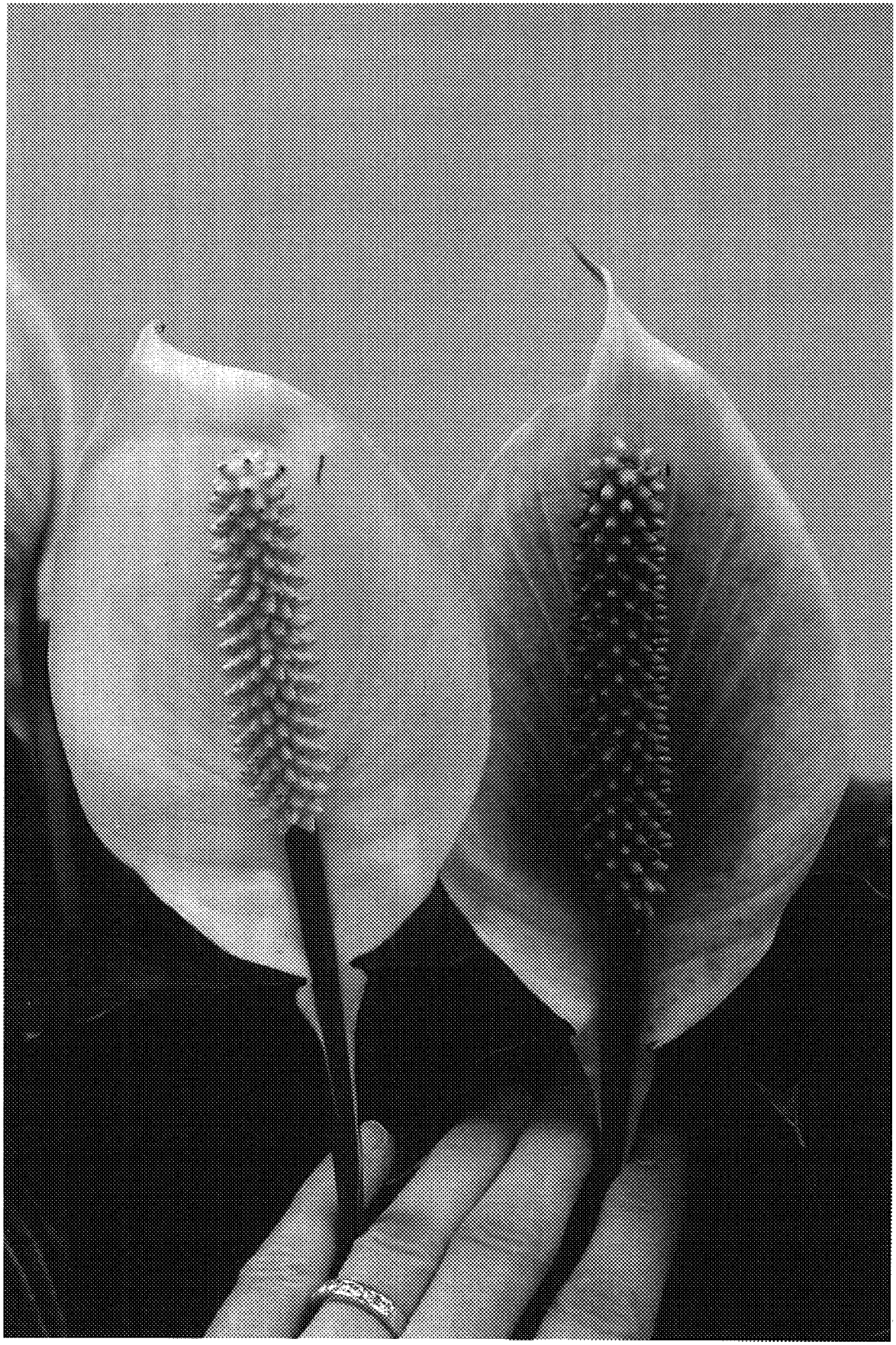

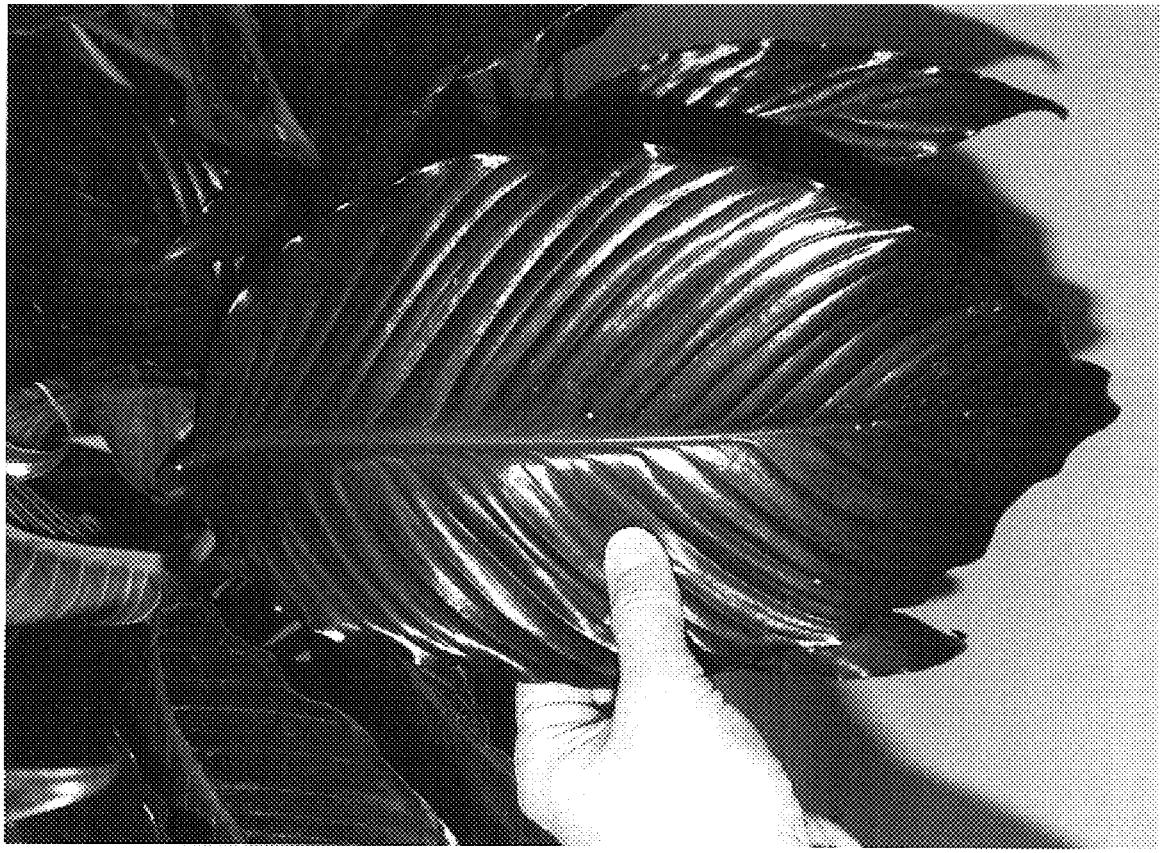
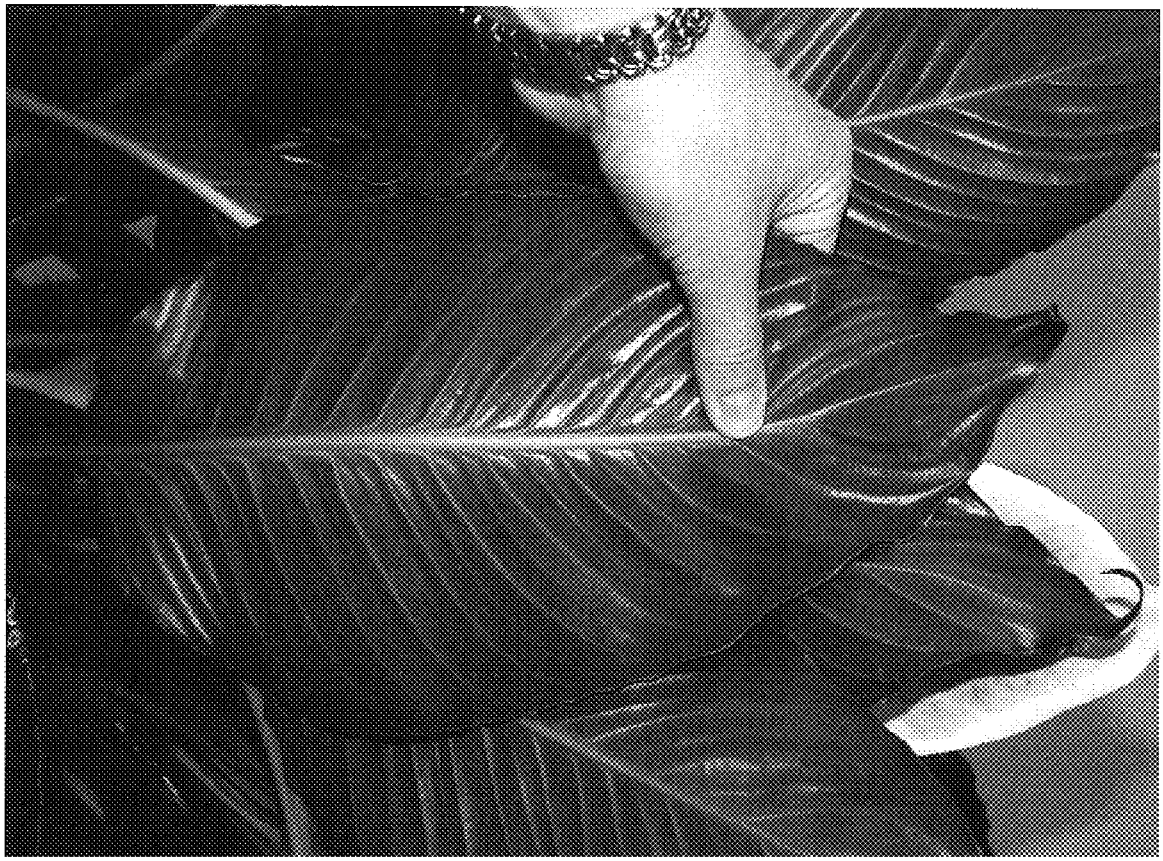

* * * * *